(12) United States Patent
Wharton

(10) Patent No.: US 7,011,840 B2
(45) Date of Patent: Mar. 14, 2006

(54) COMPOSITIONS FOR MOLE CONTROL

(75) Inventor: Steven P. Wharton, Bloomington, IN (US)

(73) Assignee: Wharton, LLC, Bloomington, IN (US)

( * ) Notice: Subject to any disclaimer, the term of this patent is extended or adjusted under 35 U.S.C. 154(b) by 75 days.

(21) Appl. No.: 10/616,110

(22) Filed: Jul. 9, 2003

(65) Prior Publication Data

US 2004/0013701 A1 Jan. 22, 2004

Related U.S. Application Data

(62) Division of application No. 09/739,983, filed on Dec. 19, 2000, now Pat. No. 6,682,752.

(51) Int. Cl.
*A01N 25/32* (2006.01)
*A01N 25/12* (2006.01)
*A01N 31/02* (2006.01)

(52) U.S. Cl. ............ 424/406; 424/405; 424/408; 424/411; 424/417; 424/421; 514/546; 514/558; 514/560

(58) Field of Classification Search .......... 424/405, 424/406, 601, 731, 84, 408, 411, 417, 421; 514/918, 920, 546, 558, 560
See application file for complete search history.

(56) References Cited

U.S. PATENT DOCUMENTS

| 631,738 A | * | 8/1899 | Dowie et al. .......... 424/601 |
|---|---|---|---|
| 2,957,804 A | | 10/1960 | Shuyler |
| 3,223,518 A | | 12/1965 | Hansen |
| 4,578,105 A | | 3/1986 | Moore |
| 4,650,665 A | | 3/1987 | Kronenthal et al. |
| 5,538,531 A | | 7/1996 | Hudson et al. |
| 5,558,889 A | | 9/1996 | Rossi |
| 5,693,344 A | | 12/1997 | Knight et al. |
| 5,756,100 A | | 5/1998 | Martinez |
| 5,985,923 A | | 11/1999 | Rossi |
| 6,025,415 A | | 2/2000 | Scholl |
| 6,139,857 A | | 10/2000 | Gaddini |

FOREIGN PATENT DOCUMENTS

JP          7076502          3/1995

OTHER PUBLICATIONS

Pease, "A New Method for Mole Control", Horticulture & Home Pest News (Aug. 11, 1995).
"Mole & Gopher Chaser Material Safety Data Sheet", Hot Pepper Wax, Inc. (Oct. 30, 2000).
Grieve, "A Modern Herbal: Castor Oil PLant", Botanical.com (Nov. 3, 2000).
Jackson, "Mole Control" (Aug., 1991).
"An Insight Into the Wonderful World of Castor Oil", Jayant Oil Mills Group (Nov. 3, 2000).
Web page for East Side Mole Works (Oct. 30, 2000).
Stewart, "When Moles Hills Become Mountains" (Oct. 30, 2000).
"Moles and Their Control", Nebguide (Oct. 30, 2000).

* cited by examiner

*Primary Examiner*—Neil S. Levy
(74) *Attorney, Agent, or Firm*—Maginot, Moore & Beck

(57) ABSTRACT

Compositions for mole control comprise an active ingredient capable of repelling moles prepared such that it can be distributed in a solid form over the mole-invaded areas.

12 Claims, No Drawings

COMPOSITIONS FOR MOLE CONTROL

This application is a divisional of U.S. application Ser. No. 09/739,983, filed on Dec. 19, 2000, now U.S. Pat. No. 6,682,752.

BACKGROUND OF THE INVENTION

The present invention relates generally to compositions for mole control that act to repel moles from treated areas. More particularly, it relates to compositions having an active ingredient that can be dispersed in a solid form onto the treated area. Preferably, the active ingredient is castor oil or any suitable castor oil derivatives.

Moles are both a nuisance and an economic pest. They dig blindly through soil creating tunnels to find food. They have a very high metabolism and must eat a lot. Therefore, they have to find a lot of food and that means a lot of digging. A mole can dig at the rate of 12–15 ft. per hour in an average garden or lawn soil.

The tunnels that moles dig in search of food are just below the surface and the digging of these tunnels severs roots and causes shrubs and other plants to decline. In addition to their surface feeding tunnels, moles also dig deeper tunnels, called runways, in which they make their nests and travel through their territory. The soil excavated from these runways is deposited on the surface in the form of mounds of loose soil called molehills. A mole or two can cause significant damage to a lawn or a garden in short order. They create ground that sinks, and cause the loss of prized perennials and bulbs. In addition, tunnels created by moles may provide travel lanes for many species of small mammals such as voles, field mice and house mice. By enhancing the habitat of other pests, moles often are indirectly responsible for damages that these rodents cause to bulbs, seeds and garden plants.

A life underground may have its reward in that moles have few natural enemies. The gardener and the landscaper have tried desperately to be a potent mole enemy, but have seemingly failed. Over the years, several methods for mole control have been attempted. For example, trapping has been one of the most effective and practical means for controlling problem moles. However, trapping takes time and practice. In addition, rather than in runways, more traps are placed in feeding tunnels where they will not catch anything.

Killing soil insects is another method that has been suggested. Controlling beetle grubs has been a standard mole control recommendation for years, but in most yards there is usually enough non-grub food remaining to keep moles thriving. Thus, moles are often present even in grub-free yards. If all the earthworms, grubs and other soil animals in a lawn are eliminated, by repeated insecticide applications, moles may be forced to seek other areas. Before moving on, however, moles may increase foraging and tunneling activity for several weeks. Moreover, the use of soil insecticides is an expensive approach, but with no immediate reduction of damage and little likelihood of long term control. In the process, soil insecticides may cause the loss of beneficial soil invertebrates and may be a hazard to desirable wildlife.

Fumigation can be used to control moles in some situations. Gas cartridges, which produce carbon monoxide and carbon dioxide when ignited, are occasionally effective. Another known fumigant is aluminum phosphide, which is a restricted use pesticide that is federally registered as a mole control. One of the drawbacks is that fumigants will generally be ineffective where soils are porous and dry, or where extensive feed tunnels are near the ground surface.

People who have been frustrated with mole damage have tried a variety of home remedies. Some of these include the use of pinwheels, windmills, rose thorns, broken glass, used cat litter, kerosene, flooding, cement or even chewing gum. Unfortunately, most home remedies fail. Several electronic devices have also been marketed, but none have proven sufficiently effective.

One method that has been proven to be effective in repelling moles is the use of a castor oil solution. A homemade concentrate can be prepared by mixing six ounces of castor oil with two tablespoons of liquid detergent in one gallon of water. This mixture is diluted at a rate of one ounce per gallon of water and applied liberally with a sprayer. In addition to the homemade formula, there are a few commercial castor oil based products that have been formulated as a mole repellant. These products are usually available in the form of liquid concentrates. The concentrates are diluted and sprayed according to the manufacturer's direction. Some of these products may successfully reduce mole activity in an area for about two months.

Nevertheless, there are some drawbacks in the application of the castor oil liquid spray. First, to be effective, castor oil solution must be thoroughly watered into the lawn. Overwatering may result in a "run off" of the solution, instead of the solution getting down into the soil where it needs to be. Second, the areas that receive extensive irrigation will quickly loose the repellant to leaching. Third, the preparation and application of the liquid castor oil may be messy. And finally, spraying of castor oil solution may wind up damaging turf plants and shrubbery or causing unsightly and smelly foliage.

A need remains for an effective mole repellant that is easy to apply and incorporated into the soil in the mole infested area Another need remains for mole repellant that stays effective for a long period of time.

SUMMARY OF THE INVENTION

In order to address the unresolved detriments of prior mole control methods, the present invention contemplates a composition for a mole control comprising an active ingredient capable of repelling moles prepared such that it can be distributed in a solid form over the mole invaded area.

In one embodiment of the present invention, the active ingredient is adsorbed on a solid matrix capable of adsorbing the active ingredient. The active ingredient preferably is castor oil. The castor oil can be a crude extract or refined oil from castor seeds.

In one feature of this embodiment, the solid matrix is any suitable adsorbent material that is capable of adsorbing the active ingredient, without substantially reducing its mole repelling effect. Otherwise, the solid matrix is capable of releasing the active ingredient such that its mole repelling effect is restored.

Preferably, the solid matrix is a coarse-grained material, which can be granular clay or fine wood chips. The solid matrix can also be a fine-grained material, which includes powdered clay.

The present invention further contemplates a composition for a slow-releasing mole control comprising an active ingredient capable of repelling moles encapsulated in an encapsulating material capable of releasing the active ingredient. The active ingredient preferably is crude or refined castor oil or any castor oil derivative that has a mole controlling effect.

In a preferred embodiment, the active ingredient is in a substantially liquid form. The active ingredient is captured in the encapsulating material, which preferably is a solid or can be dried into a solid form. The encapsulating material can be any suitable naturally occurring material or synthetic material.

In another preferred embodiment, the active ingredient is in a solid form encapsulated in a solid encapsulating material. The solid active ingredient can be a castor oil derivative or salt. Alternatively, the liquid castor oil can be adsorbed onto a solid matrix, prior to the encapsulation.

Further, the present invention includes a method for making compositions for slow-releasing mole control. The method comprises the step of providing the active ingredient and the encapsulating material, mixing the encapsulating material with the active ingredient such that the encapsulating material completely coats the active ingredient. The method may include transforming the active ingredient into a solid form prior to mixing with the encapsulating material. In addition, the method may also include the step of drying the encapsulating material.

The step of transforming the active ingredient into a solid form may include the step of providing a solid matrix capable of adsorbing the active material thereon, and adsorbing the active ingredient onto the solid matrix.

It is one object of the present invention to provide a solid form of mole repellant. Another objective is to provide a mole repellant that is effective for a relatively long period of time.

One further benefit is achieved by features of the invention that permit easy application and incorporation in the soil. These and other objects and benefits of the invention will be made clear upon consideration of the following written description.

DESCRIPTION OF THE PREFERRED EMBODIMENTS

For the purpose of promoting an understanding of the principles of the invention, the embodiments of the present invention will be described in detail. It will nevertheless be understood that no limitation of the scope of the invention is thereby intended. The invention includes any alterations and further modifications in the described compositions and methods and further applications of the principles of the invention which would normally occur to one skilled in the art to which the invention relates.

The present invention contemplates a composition for a mole control, preferably by means of repelling moles from a treated area such as a garden, a yard or a turf. The composition is prepared such that the composition is a solid form.

In one embodiment of the present invention, the composition comprises an active ingredient capable of repelling moles and a solid matrix on which the ingredient is adsorbed. Preferably, the active ingredient is castor oil. In order for the castor oil or other active ingredient to be capable of repelling moles, the effective amount of castor oil or other active ingredients in the present composition should be equivalent to the castor oil of between 65% USP and 100% USP. The castor oil can be a crude extract or refined oil from castor seeds. It does not matter how the oil is extracted from the seeds as long as the oil retains the mole repelling effect. The active ingredient can be hydroxy-, unsaturated C-18 fatty acid-ricinoleic acid, which is a major component of castor oil. Other derivatives of castor oil, particularly those that have a mole repelling effect can also be used as the active ingredient. Examples of the castor oil derivatives include hydrogenated castor oil, 12-hydroxy steric acid, undecylenic acid, or ricinoleic acid. It is also contemplated that the active ingredient may be any other natural or synthetic material that has a repelling effect on motes. The examples of the natural material are the extract from roots of castor oil or the extract from "mole plant" (or gopher purge *Euphorbia latthyris*).

Another feature of this embodiment includes the solid matrix that is capable of adsorbing the active ingredient. It is desirable to use adsorbing material that has high adsorbing capacity. A suitable solid matrix is a coarse-grained material. The coarse-grained material should be substantially uniform in size to affect the uniformity of adsorbed active ingredient, and consequently affects the uniformity of the repellant application in the mole-infested area. Preferably, the coarse-grained material is a granular clay material commonly referred to as "kitty litter". Other suitable coarse-grained materials include fine wood chips, sawdust, straw dust, grass pellets, or fertilizer pellets. Another suitable solid matrix is a fine-grained material that is capable of uniformly adsorbing the active ingredient. Preferably, the fine-grained material is powdered clay. Of course, any other suitable fine-grained material such as flour or bone or eggshell powder can also be used. In addition to the naturally occurring material, the solid matrix can also include other synthetic materials, preferably biodegradable materials.

In the embodiment described above, the active ingredient preferably retains the repelling effect after the adsorption onto the solid matrix. However, if the active ingredient loses some of its repelling effect when it is adsorbed onto the solid matrix, the solid matrix is capable of releasing the active ingredient to restore the mole repelling effect. This releasing mechanism preferably can be enhanced by hydrolysis. In this way, the active ingredient is released into the soil by repeat watering.

The present invention further contemplates a method for making a composition for mole control. The method includes mixing suitable proportions of the active ingredient and the solid matrix together into a uniform mixture. To mix the Individual components together, a machine-operated mixer may be used. Of course, if feasible, a hand-mixer can also be used. The solid matrix should be put in the mixer first, and while the mixer is in the mixing mode, the active ingredient is added slowly until a uniform mixture is formed. It is important to avoid adding too much liquid active ingredient like castor oil because the mixture may turn too clumping. It is desirable to have clumps of the size of small peas, and not too much larger.

Alternatively, the composition can be made by soaking the solid matrix such as fine wood chips in the active ingredient until the adsorbing process ends. Then the excess active ingredient is removed and the mixture is dried. The mixture can also be sieved through a sizing screen for uniformity.

The method may include adding other non-active ingredients that improve the attachment of the active ingredient to the surface of the solid matrix, or adding ingredients that enhance the release of the active ingredient from the solid matrix. For example, water may be added to the solid matrix in order to increase the adsorbing ability or powdered detergent may be included in the composition that has castor oil as the active ingredient. The detergent can help the castor oil to better disperse in water, thus improving the distribution of the oil into the treated soil. Alternatively, a suitable detergent may be added to the irrigation water to extract the castor oil from the solid matrix such that it spreads more evenly in the treated soil.

Further, the present invention contemplates a composition for a slow-releasing mole control. The composition comprises an active ingredient capable of repelling moles, and an encapsulating material for encapsulating and releasing the active ingredient. The active ingredient preferably is crude or refined castor oil or castor oil derivatives.

In a preferred embodiment, the active ingredient is in a substantially liquid form. The active ingredient is captured in the encapsulating material, which preferably is a solid or can be dried into a solid form. Moreover, the encapsulating material is capable of being hydrolyzed or broken down to slowly release the active ingredient into the soil. The encapsulating material can be any suitable naturally occurring material or synthetic material. The naturally occurring material can be clay powder, or certain castor oil derivatives. The synthetic material can be a soluble polymer.

In another preferred embodiment, the active ingredient is in a solid form. If the active ingredient originally is in a liquid form, a solidification process can be accomplished by means of a series of chemical reactions to yield a solid salt that still maintains the mole repelling effect. The solidified active ingredient is captured in the encapsulating material capable of releasing the active ingredient to repel the moles.

In yet another preferred embodiment, the active ingredient is adsorbed onto a solid matrix capable of adsorbing the active ingredient. The solid matrix can be a coarse-grain material such as granular clay or wood chips, or fine-grained material such as powdered clay or powdered wood. The mixture of adsorbed active ingredient and the solid matrix is encapsulated in an encapsulating material, which can slowly release the active ingredient.

The present invention further includes a method for making the composition for a slow-releasing mole control. The method comprises the step of providing the active ingredient capable of repelling moles, and an encapsulating material; transforming the active ingredient into a solid form; mixing the encapsulating material with the solidified active ingredient such that the encapsulating material completely coats the active ingredient. The method may also include the step of drying the encapsulating material.

Transforming the active ingredient into a solid form may include the step of providing a solid matrix capable of adsorbing the active material thereon, and adsorbing the active ingredient onto the solid matrix thereon. Alternatively, the step of transforming the active ingredient into a solid form may include a temporary modification of the physical property of the active ingredient, which may involve reducing temperature to a freezing temperature.

Moreover, the present invention contemplates the addition of other non-active ingredients to the composition for mole control in order to enhance the adsorption of the active ingredient onto the solid matrix, or to enhance the release or the spread of the active ingredient into the soil. For example, any suitable detergent may be added to the composition containing castor oil as the active ingredient so that it can be solubilized and better distributed when the water is added to the soil.

The composition can be applied to mole infested areas by hand spreading or by using a mechanical spreader. Any mechanical spreader commonly used for applying a fertilizer may be used. The composition may also be tilled or incorporated into the soil so that it is placed closer the runway in which the mole makes its nest. In addition, irrigation may be helpful in facilitate the disbursement of the composition or the active ingredient in the soil, thus increases mole repelling effect.

While the invention has been described in detail in the foregoing description, the same is to be considered as illustrative and not restrictive in character. It should be understood that only the preferred embodiments have been described and that all changes and modifications that come within the spirit of the invention are desired to be protected.

For example, the composition may include the active ingredient adsorbed onto a solid matrix that is made in the form of strips that can be laid down in the soil along the mole tunnels or inserted right in the mole tunnels. In addition, the composition of this invention can also be applied in combination with insect controls or other mole control measures.

What is claimed is:

1. A method for controlling moles within an area, comprising the steps of:
    (a) providing a composition for mole control having an active ingredient capable of repelling moles adsorbed on an inert solid matrix capable of adsorbing the active ingredient, the composition including an active ingredient capable of repelling moles adsorbed on an inert solid matrix capable of adsorbing said active ingredient forming a substantially uniform mixture; and
    (b) applying the composition to the soil of the area, wherein the inert solid matrix is a granular material consisting essentially of at least one of granular clay, sawdust, straw, grass pellets, and wood chips, and further wherein said active ingredient includes at least one of hydrogenated castor oil, 12-hydroxy steric acid, undecylenic acid, ricinoleic acid, and extract from castor plant parts.

2. The method of claim 1 wherein said composition further comprises an encapsulating material capable of controlling release of active ingredient, said encapsulating material disposed on an outer surface of said active ingredient adsorbed on said inert solid matrix.

3. The method of claim 1 wherein said active ingredient includes castor oil.

4. The method of claim 1, wherein said applying step is performed using a mechanical spreader.

5. The method of claim 1 further comprising the step of:
    (c) mixing the composition into soil.

6. The method of claim 5 further comprising the step of:
    (d) applying water to the composition to facilitate disbursement of the active ingredient in the soil.

7. A method for controlling moles within an area, comprising the steps of:
    (a) providing a composition for mole control having an active ingredient capable of repelling moles adsorbed on an inert solid matrix capable of adsorbing the active ingredient, the composition including an active ingredient capable of repelling moles adsorbed on an inert solid matrix capable of adsorbing said active ingredient forming a substantially uniform mixture; and
    (b) applying the composition to the soil of the area, wherein the inert solid matrix is a powdered material consisting essentially of at least one of clay powder, eggshell powder, bone powder, and flour, and further wherein said active ingredient includes at least one of hydrogenated castor oil, 12-hydroxy steric acid, undecylenic acid, ricinoleic acid, and extract from castor plant parts.

8. The method of claim 7 wherein said composition further comprises an encapsulating material capable of controlling release of the active ingredient, the encapsulating material disposed on an outer surface of the active ingredient adsorbed on the inert solid matrix.

9. The method of claim 7 wherein the active ingredient includes castor oil.

10. The method of claim 7, wherein said applying step is performed using a mechanical spreader.

11. The method of claim 7 further comprising the step of:
(c) mixing the composition into soil.

12. The method of claim 11 further comprising the step of:

(d) applying water to the composition to facilitate disbursement of the active ingredient in the soil.

* * * * *

UNITED STATES PATENT AND TRADEMARK OFFICE
CERTIFICATE OF CORRECTION

PATENT NO. : 7,011,840 B2 Page 1 of 1
APPLICATION NO. : 10/616110
DATED : July 9, 2003
INVENTOR(S) : Steven P. Wharton It is certified that error appears in the above-identified patent and that said Letters Patent is hereby corrected as shown below:

Column 4, line 6: replace "motes" with --moles--

Signed and Sealed this

Seventh Day of November, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,011,840 B2 | Page 1 of 1 |
| APPLICATION NO. | : 10/616110 | |
| DATED | : March 14, 2006 | |
| INVENTOR(S) | : Steven P. Wharton | |

It is certified that error appears in the above-identified patent and that said Letters Patent is hereby corrected as shown below:

Column 4, line 6: replace "motes" with --moles--

This certificate supersedes Certificate of Correction issued November 7, 2006.

Signed and Sealed this

Twelfth Day of December, 2006

JON W. DUDAS
*Director of the United States Patent and Trademark Office*